United States Patent [19]
Kato et al.

[11] 4,166,180
[45] Aug. 28, 1979

[54] 2-ARYLPIPERAZINE DERIVATIVES AND THE PREPARATION THEREOF

[75] Inventors: Hideo Kato; Eiichi Koshinaka; Nobuo Ogawa, all of Fukui, Japan

[73] Assignee: Hokuriku Pharmaceutical Co., Ltd., Fukui, Japan

[21] Appl. No.: 795,869

[22] Filed: May 11, 1977

[30] Foreign Application Priority Data

May 13, 1976 [JP] Japan .................................. 51-53865

[51] Int. Cl.² ........................................... C07D 241/12
[52] U.S. Cl. .................................... 544/398; 544/377; 544/403
[58] Field of Search .................... 260/268 R; 544/398, 544/401, 403, 377

[56] References Cited
PUBLICATIONS
Roderick et al., J. Med. Chemistry 9(2), 181–185, (1966).

Primary Examiner—Jose Tovar
Attorney, Agent, or Firm—Burgess, Ryan and Wayne

[57] ABSTRACT

A process is provided for preparing 2-arylpiperazine derivatives and more particularly, 2-phenylpiperazine derivatives of the formula

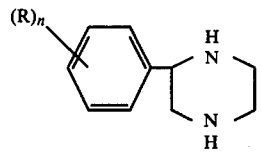

wherein R represents a group selected from the group consisting of a halogen atom, a lower alkyl group (having carbon atoms of 1 to about 8, preferably 1 to 4), a lower alkoxy group (having carbon atoms of 1 to about 8, preferably 1 to 4), a nitro group, a cyano group, a benzyloxy group, a hydroxy group and when n is 2 R is a methylenedioxy group, and n represents 1, 2 or 3.

5 Claims, No Drawings

2-ARYLPIPERAZINE DERIVATIVES AND THE PREPARATION THEREOF

The present invention relates to 2-arylpiperazine derivatives, more particularly to 2-phenylpiperazine derivatives represented by the formula:

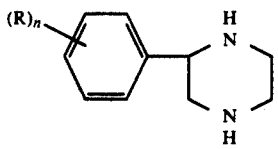

wherein R represents a group selected from the group consisting of a halogen atom, a lower alkyl group (having carbon atoms of 1 to about 8, preferably 1 to 4), a lower alkoxy group (having carbon atoms of 1 to about 8, preferably 1 to 4), a nitro group, a cyano group, a benzyloxy group, a hydroxy group and when N is 2 R is a methylenedioxy group and n represents 1, 2 or 3; and a process for producing the same.

The processes for producing 2-phenylpiperazine are reported in J. Med. Chem. 9, 181–185 (1966) and J. Am. Chem. Soc., 69, 854–855 (1947). However, these processes are objectionable in that many steps are required, the procedures are complicated and the yield is poor. In addition, no description is found disclosing any compound having substituents on the phenyl group thereof.

As a result of the investigations, the inventors have found a process for reducing a phenylglyoxal represented by the formula:

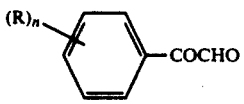

wherein R and n each is as defined above, in the presence of ethylene diamine and thus the present invention has been accomplished.

The present invention is advantageous in that the compounds having substituents on the phenyl group thereof can easily be prepared. Of course, 2-phenylpiperazine per se can be successfully prepared in accordance with the process of the present invention.

The compounds of the present invention are prepared by reducing a phenyl glyoxal derivative represented by the formula II above or a hydrate thereof, in the presence of ethylenediamine represented of the formula III:

In the case that the compounds of the present invention have a benzyl substituent(s) on the phenyl group thereof, debenzylation is subsequently carried out, if necessary.

In more detail, the compounds represented by the formula II are condensed with an equimolar or excess amount of ethylene diamine in an organic solvent, followed by reduction. Preferred examples of organic solvents include alcohols such as methanol, ethanol, etc. The condensation reaction can also be carried out at elevated temperature, but, in general, room temperature is sufficient.

Thereafter, reduction is conducted by adding a reducing agent such as sodium borohydride (NaBH$_4$), etc.

It is preferred that the reaction temperature be at 0° C. to room temperature (about 25° C.).

Of the thus prepared 2-arylpiperazine derivatives, the compounds having a benzyloxy group(s) on the phenyl group thereof can be converted to compounds having a hydroxy group(s) on the phenyl group thereof by hydrogenating in the presence of a catalyst such as palladium-carbon (Pd-C), etc. thereby to proceed with debenzylation.

The phenyl glyoxal derivatives represented by the formula II which are a starting material of the present invention can easily be prepared by oxidizing an acetophenone derivative represented by the formula IV:

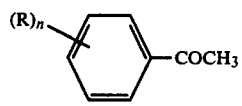

wherein n and R each represents the same meaning as defined above, with selenium dioxide(SeO$_2$).

Typical examples of the compounds represented by the formula I include, for example:
(1) 2-(2-Chlorophenyl)piperazine
(2) 2-(2-Methoxyphenyl)piperazine
(3) 2-(3-Benzyloxyphenyl)piperazine
(4) 2-(3-Nitrophenyl)piperazine
(5) 2-(4-Cyanophenyl)piperazine
(6) 2-(4-Fluorophenyl)piperazine
(7) 2-(4-Tolyl)piperazine
(8) 2-(3,4-Dimethoxyphenyl)piperazine
(9) 2-(3,4-Methylenedioxyphenyl)piperazine
(10) 2-(3-Bromo-4-methoxyphenyl)piperazine
(11) 2-(4-Benzyloxy-3-methoxyphenyl)piperazine
(12) 2-(3,5-Dibenzyloxyphenyl)piperazine
(13) 2-(2,3,4-Trimethoxyphenyl)piperazine
(14) 2-(3,4,5-Trimethoxyphenyl)piperazine
(15) 2-(3-Hydroxyphenyl)piperazine
(16) 2-(4-Hydroxyl-3-methoxyphenyl)piperazine
(17) 2-(4-Methylphenyl)piperazine
(18) 2-(3-Bromophenyl)piperazine
(19) 2-(3-Methoxy-4-hydroxyphenyl)piperazine
(20) 2-(2-Benzyloxyphenyl)piperazine
(21) 2-(4-Benzyloxyphenyl)piperazine
(22) 2-(2-Hydroxyphenyl)piperazine
(23) 2-(4-Hydroxyphenyl)piperazine
(24) 2-(2,4-Dibenzyloxyphenyl)piperazine
(25) 2-(3,4-Dibenzyloxyphenyl)piperazine
(26) 2-(3,4,5-Tribenzyloxyphenyl)piperazine
(27) 2-(2,4-Dihydroxyphenyl)piperazine
(28) 2-(3,4-Dihydroxyphenyl)piperazine
(29) 2-(3,4,5-Trihydroxyphenyl)piperazine Of these compounds, Compounds (2), (8), (13), (14), (15), (22), (23), (27), (28) and (29) are particularly preferred.

It has been confirmed from a nuclear magnetic resonance spectrum (NMR) that the 2-aryl group, especially the 2-phenyl group, in the 2-arylpiperazine derivatives obtained in accordance with the present invention, have an equatorial configuration.

The compounds represented by the formula I which are prepared in accordance with the present invention may be converted to acid addition salts thereof in a conventional manner, using an inorganic acid (hydrochloric acid, sulfuric acid, nitric acid, etc.) or an organic acid (oxalic acid, maleic acid, fumaric acid, tartaric acid, etc.).

The compounds of the present invention which are represented by the formula I have analgetic, vasodilatory, antispasmodic actions and action on circulatory systems, and are useful as drugs as well as intermediates for drugs having the aforementioned activities.

The present invention will be explained in detail with reference to the examples hereinbelow.

SYNTHESIS OF STARTING MATERIAL

3-Benzyloxyphenyl glyoxal

To a solution of 9.4 g. of selenium dioxide in a solvent mixture of 50 ml. of dioxane and 1.7 ml. of water, was added 16.5 g. of 3-benzyloxyacetophenone. The mixture was refluxed for 4 hrs. with stirring. The resulting precipitates were removed by filtration and the solvents were distilled off from the filtrate under reduced pressure. The residue was dissolved in benzene and washed with water several times. After drying the benzene layer, benzene was removed by distillation to obtain the glyoxal as yellow liquid in a quantitative yield.

EXAMPLE 1

2-(3-Benzyloxyphenyl)piperazine

The glyoxal obtained as above was dissolved in a mixture of 180 ml. of methanol and 30 ml. of benzene. To the solution, 5.25 g. of anhydrous ethylene diamine was added with stirring. After stirring for a further 30 mins. at room temperature, 4.2 g. of sodium borohydride was added to the mixture little by little under ice cooling. After the completion of the addition, stirring was continued for 1.5 hr. at room temperature. To the residue obtained by removing the solvent, water was added to dissolve the residue. The aqueous solution was extracted with chloroform. The chloroform layer was washed with water and dried.

After the solvent was distilled off, the residue was dissolved in ethanol. Ethereal hydrochloric acid was added to the solution to convert the product to the hydrochloride, which was recrystallied from water-ethanol to obtain 127 g. of the product having a melting point of 237°–239° C.

Elemental Analysis $C_{17}H_{20}N_2O \cdot 2HCl$. Calcd.—C: 59.83, H: 6.50, N: 8.21. Found—C: 59.59, H: 6.48, N: 8.03. Free base: m.p. 52°–54° C.

NMR (in $CdCl_3$):8.25 (2H, singlet, NH×2), 7.36 (1H, doublet-doublet, J=125; 10 Hz, $C^3$-Hax), 7.3–6.8 (5H, multiplet, $C^3$-Heq, $C^5$—$H_2$, $C^6$—$H_2$), 6.31 (1H, doublet-doublet, J=10; 3.5 Hz, $C^2$-Hax), 4.99 (2H, singlet, Ph—$CH_2$) Mass m/e: 268(M+), 225, 134 (base), 91, 44.

EXAMPLE 2

2-(3,4-Methylenedioxyphenyl)piperazine

In 40 ml. of methanol was dispersed 4.9 g. of the glyoxal monohydrate which was obtained by oxidizing 3',4'-methylenedioxyacetophenone with selenium dioxide in a manner similar to the Synthesis of Example 1. To the dispersion, 1.8 g. of anhydrous ethylene diamine was added with stirring. After allowing to stand for 30 mins. at room temperature, 1.43 g. of sodium borohydride was added to the mixture little by little under ice cooling. After the completion of the addition, the mixture was stirred overnight. After the solvent was distilled off, the resulting residue was dissolved in water. The aqueous solution was extracted with chloroform. The chloroform layer was washed with water and dried. The residue which was obtained by distilling the solvent off was recrystallized from ethyl acetate to obtain 3.3 g. of the product showing a melting point of 126°–128° C.

Elemental Analysis: $C_{11}H_{14}N_2O_2$. Calcd. C: 64.06, H: 6.84, N: 13.58. Found C: 63.80, H: 6.88, N: 13.81. Dihydrochloride: m.p. 268°–270° C. (decomposed)

NMR (in $CdCl_3$): 8.25 (2H, singlet, NH×2) 7.40 (1H, doublet-doublet, J=125, 10 Hz, $C^3$-Hax), 7.3–6.8 (5H, multiplet, $C^3$-Heq, $C^5$—$H_2$, $C^6$—$H_2$), 6.37 (1H, doublet-doublet, J=10; 3.5 Hz, $C^2$-Hax), 4.11 (2H, singlet, —$OCH_2O$—). 3.3–3.1 (3H, multiplet, Ar—H).

Mass m/e: 206 (M+), 163 (base), 162, 44.

In a manner similar to Examples 1 and 2, the following compounds were obtained.

(i) 2-(2-Chlorophenyl)piperazine.dihydrochloride: m.p. 279°–282° C.

(ii) 2-(2-Methoxyphenyl)piperazine: m.p. 74°–75° C. dihydrochloride: m.p. 283°–285° C. (decomposed)

(iii) 2-(3-Nitrophenyl)piperazine: m.p. 81°–83° C. dihydrochloride: m.p. 258°–262° C. (decomposed)

(iv) 2-(4-Tolyl)piperazine: m.p. 97° C. dihydrochloride: m.p. above 300° C.

(v) 2-(4-Fluorophenyl)piperazine: m.p. 110°–112° C. dihydrochloride: m.p. above 300° C.

(vi) 2-(4-Cyanophenyl)piperazine: m.p. 106°–108° C. dihydrochloride: m.p. 274°–277° C. (decomposed)

(vii) 2-(3-Bromo-4-methoxyphenyl)piperazine: m.p. 72°–73° C. dihydrochloride: m.p. 267°–270° C.(decomposed)

(viii) 2-(3,4-Dimethoxyphenyl)piperazine: m.p. 44°–46° C. dihydrochloride: m.p. 266°–268° C.(decomposed)

(ix) 2-(3-Methoxy-4-benzyloxyphenyl)piperazine: m.p. 95°–97° C. dihydrochloride: m.p. 259°–261° C.(decomposed)

(x) 2-(3,5-Dibenzyloxyphenyl)piperazine: m.p. 97°–98° C. dihydrochloride: m.p. 232°–234° C.

(xi) 2-(2,3,4-Trimethoxyphenyl)piperazine: m.p. 63° C. dihydrochloride: m.p. 255°–258° C.(decomposed)

(xii) 2-(3,4,5-Trimethoxyphenyl)piperazine: m.p. 93° C. dihydrochloride: m.p. 270°–273° C.(decomposed)

(xiii) 2-(2-Benzyloxyphenyl)piperazine: m.p. 91.5°–92.5° C. dihydrochloride: m.p. 232°–234° C.

(xiv) 2-(4-Benzyloxyphenyl)piperazine: m.p. 125.5°–127° C. dihydrochloride: m.p. 244°–246° C.(decomposed)

(xv) 2-(2,4-Dibenzyloxyphenyl)piperazine: dihydrochloride: m.p. 237°–240° C.

(xvi) 2-(3,4-Dibenzyloxyphenyl)piperazine: m.p. 83°–84.5° C. dihydrochloride: m.p. 224°–246° C.

(xvii) 2-(3,4,5-Tribenzyloxyphenyl)piperazine: m.p. 91°–93° C.

EXAMPLE 3

2-(3-Hydroxyphenyl)piperazine dihydrochloride

In 100 ml. of water was dissolved 2.0 g. of 2-(3-benzyloxyphenyl)piperazine. The solution was subjected to hydrogenation for 4 hrs. under pressure with heating (50° C.), using as a catalyst 500 mg. of 5% palladium-carbon. After the catalyst was removed, the solvent was distilled off. The residue was dissolved in water-ethanol to crystallize. The product having a melting point of 260°–264° C. (decomposed) was obtained in an amount of 1.4 g.

Mass m/e: 178 (M+), 135, 134, 44, 38, 36.

In a manner similar to Example 3, the following compounds were obtained.

(xviii) 2-(4-Hydroxy-3-methoxyphenyl)piperazine dihydrochloride: m.p. 264°–266° C. (decomposed)

(xix) 2-(2-Hydroxyphenyl)piperazine: dihydrochloride: m.p. 232°–234° C. (decomposed)

(xx) 2-(4-Hydroxyphenyl)piperazine dihydrochloride: m.p. 258°–260° C.(decomposed)

(xxi) 2-(2,4-Dihydroxyphenyl)piperazine: dihydrochloride: m.p. 251°–255° C. (decomposed)

(xxii) 2-(3,4-Dihydroxyphenyl)piperazine: dihydrochloride: m.p. 251°–254° C. (decomposed)

(xxiii) 2-(3,4,5-Trihydroxyphenyl)piperazine: dihydrochloride: m.p. 276°–280° C. (decomposed)

What is claimed is:

1. A process for producing a 2-arylpiperazine derivative represented by the formula:

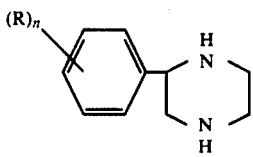

wherein n represents 1, 2 or 3; and R represents a member selected from the group consisting of a halogen atom, a lower alkyl group having from 1 to 8 carbon atoms, a lower alkoxy group having from 1 to about 8 carbon atoms, a nitro group, a cyano group, a benzyloxy group, a hydroxy group or a methylenedioxy group, which comprises reducing a phenyl glyoxal derivative represented by the formula

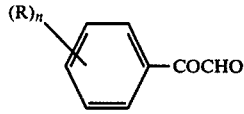

wherein n and R each has the same meaning as defined above, in the presence of ethylenediamine represented by the formula:

$H_2NCH_2CH_2NH_2$.

2. The process of claim 1 wherein sodium borohydride is employed as a reducing agent.

3. The process of claim 1 wherein R represents a benzyloxy group(s), further comprising debenzylating said derivative.

4. The process of claim 1 wherein each of said lower alkyl and lower alkoxy groups have from 1 to 4 carbon atoms.

5. The process of claim 4 wherein R is methoxy or hydroxy.

* * * * *